United States Patent
Rao et al.

(10) Patent No.: US 8,377,327 B2
(45) Date of Patent: Feb. 19, 2013

(54) TETRAFLUOROPROPENE PRODUCTION PROCESSES

(75) Inventors: Velliyur Nott Mallikarjuna Rao, Wilmington, DE (US); Mario Joseph Nappa, Newark, DE (US); Allen Capron Sievert, Elkton, MD (US); Ralph Newton Miller, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 128 days.

(21) Appl. No.: 12/758,839

(22) Filed: Apr. 13, 2010

(65) Prior Publication Data

US 2010/0200798 A1   Aug. 12, 2010

Related U.S. Application Data

(63) Continuation-in-part of application No. 12/301,070, filed as application No. PCT/US2007/014645 on Jun. 22, 2007, now Pat. No. 7,722,781.

(60) Provisional application No. 60/816,650, filed on Jun. 27, 2006.

(51) Int. Cl.
    *C09K 5/04* (2006.01)

(52) U.S. Cl. .......... 252/67; 570/155; 570/156; 510/177; 510/408

(58) Field of Classification Search .................... 252/67; 570/155, 156; 510/177, 408
    See application file for complete search history.

(56) References Cited

U.S. PATENT DOCUMENTS

| | | | |
|---|---|---|---|
| 5,396,000 A | 3/1995 | Nappa et al. | |
| 5,679,875 A | 10/1997 | Aoyama et al. | |
| 5,716,590 A | 2/1998 | Roewer et al. | |
| 5,856,593 A | 1/1999 | Powell et al. | |
| 6,031,141 A | 2/2000 | Mallikarjuna et al. | |
| 7,189,884 B2 | 3/2007 | Mukhopadhyay et al. | |
| 7,230,146 B2 | 6/2007 | Merkel et al. | |
| 7,279,451 B2 | 10/2007 | Singh et al. | |
| 7,345,209 B2 | 3/2008 | Mukhopadhyay et al. | |
| 7,423,188 B2 | 9/2008 | Miller et al. | |
| 7,485,760 B2 * | 2/2009 | Wang et al. | 570/236 |
| 7,534,366 B2 * | 5/2009 | Singh et al. | 252/68 |
| 7,592,494 B2 * | 9/2009 | Tung et al. | 570/164 |
| 7,663,007 B2 * | 2/2010 | Rao et al. | 570/156 |
| 7,722,781 B2 * | 5/2010 | Rao et al. | 252/67 |
| 7,897,823 B2 * | 3/2011 | Miller et al. | 570/155 |
| 7,982,073 B2 * | 7/2011 | Nappa et al. | 570/156 |
| 2004/0256594 A1 | 12/2004 | Singh et al. | |
| 2006/0094911 A1 * | 5/2006 | Rao et al. | 570/155 |
| 2006/0106263 A1 * | 5/2006 | Miller et al. | 570/155 |
| 2006/0116538 A1 * | 6/2006 | Miller et al. | 570/178 |
| 2007/0100175 A1 | 5/2007 | Miller et al. | |
| 2007/0179324 A1 | 8/2007 | Van Der Puy et al. | |
| 2008/0011678 A1 * | 1/2008 | Knapp | 210/634 |
| 2008/0051610 A1 * | 2/2008 | Wang et al. | 570/156 |
| 2008/0051611 A1 * | 2/2008 | Wang et al. | 570/166 |
| 2009/0099395 A1 * | 4/2009 | Sakyu et al. | 570/156 |
| 2009/0118554 A1 * | 5/2009 | Rao et al. | 570/156 |
| 2010/0025620 A1 | 2/2010 | Nappa et al. | |
| 2010/0185027 A1 * | 7/2010 | Wang et al. | 570/151 |
| 2010/0185029 A1 * | 7/2010 | Elsheikh et al. | 570/157 |

FOREIGN PATENT DOCUMENTS

| | | |
|---|---|---|
| EP | 0974571 B1 | 1/2000 |
| FR | 2729136 A1 | 7/1996 |
| WO | 94/27940 A1 | 12/1994 |
| WO | 2005108334 A1 | 11/2005 |
| WO | 2007019355 A1 | 2/2007 |
| WO | 2007053689 A2 | 5/2007 |
| WO | 2008/002499 A2 | 1/2008 |
| WO | 2008/002501 A2 | 1/2008 |
| WO | 2008/040969 A2 | 4/2008 |

OTHER PUBLICATIONS

CAS reg. No. 29118-25-0, Nov. 16, 1984.*
U.S. Appl. No. 12/301,077, filed Nov. 17, 2008, Rao et al.
U.S. Appl. No. 12/301,065, filed Nov. 17, 2008, Rao et al.
"Radiation-Induced Polymerization at High Pressure of Cis- and Trans-1,3,3,3-Tetrafluoropropene in Bulk and with Tetrafluoroethylene", by Daniel W. Brown, Robert E. Lowry, and Leo A. Wall, in the "Journal of Polymer Science": Polymer Chemistry Edition, vol. 11, 1973-1984 (1973).

* cited by examiner

*Primary Examiner* — Douglas McGinty

(57) ABSTRACT

A process is disclosed for the manufacture of $CF_3CF=CH_2$ and $CF_3CH=CHF$. The process involves dehydrofluorinating $CF_3CHFCH_2F$ in the presence of a dehydrofluorination catalyst to produce a product mixture comprising $CF_3CF=CH_2$ and $CF_3CH=CHF$, and recovering said $CF_3CF=CH_2$ and $CF_3CH=CHF$ from the product mixture. The present invention also provides a composition comprising (a) the Z-isomer of $CF_3CH=CHF$ and (b) HF; wherein the HF is present in an effective amount to form an azeotropic combination with the Z—$CF_3CH=CHF$.

3 Claims, No Drawings

TETRAFLUOROPROPENE PRODUCTION PROCESSES

CROSS-REFERENCE TO RELATED APPLICATION

This application is a Continuation-in-Part of application Ser. No. 12/301,070 filed Nov. 17, 2008 and issued as U.S. Pat. No. 7,722,781, which represents a national filing under 35 USC 371 of International Application No. PCT/US2007/014645 filed Jun. 22, 2007, claiming priority of U.S. Provisional Application No. 60/816,650 filed Jun. 27, 2006.

FIELD OF THE INVENTION

The present invention relates to the production of tetrafluoropropenes and more specifically to the production of 2,3,3,3-tetrafluoropropene (HFC-1234yf) and 1,3,3,3-tetrafluoropropene (HFC-1234ze) from 1,1,1,2,3-pentafluoropropane (HFC-245eb). The present invention also relates to the azeotrope or near azeotrope compositions of Z-HFC-1234ze and HF.

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

HFC-1234yf and HFC-1234ze, both having zero ozone depletion potential and low global warming potential, have been identified as potential refrigerants. U.S. Patent Publication No. 2006/0106263 A1 discloses the separate production of HFC-1234ze (mixture of E- and Z-isomers) by a catalytic vapor phase dehydrofluorination of $CF_3CH_2CHF_2$ and of HFC-1234yf by a catalytic vapor phase dehydrofluorination of $CF_3CF_2CH_3$.

There is a need for new manufacturing processes for the production both HFC-1234yf and HFC-1234ze.

SUMMARY OF THE INVENTION

The present invention provides a process for the manufacture of HFC-1234yf and HFC-1234ze. The process comprises (a) dehydrofluorinating HFC-245eb in the presence of a dehydrofluorination catalyst to produce a product mixture comprising HFC-1234yf and HFC-1234ze; and (b) recovering said HFC-1234yf and HFC-1234ze from the product mixture produced in (a).

The present invention also provides a composition comprising (a) the Z-isomer of HFC-1234ze and (b) HF; wherein the HF is present in an effective amount to form an azeotropic combination with the Z-HFC-1234ze.

DETAILED DESCRIPTION

The present invention provides a process to produce HFC-1234yf and HFC-1234ze by the dehydrofluorination of HFC-245eb. HFC-1234ze can exist as one of two configurational isomers, E or Z. HFC-1234ze as used herein refers to a single configurational isomer or a mixture of the isomers. HFC-245eb can be prepared by the hydrogenation of $CF_3CClFCCl_2F$ (CFC-215bb) over a palladium on carbon catalyst as disclosed in U.S. Publication No. 2009/0264690 A1, incorporated herein in its entirety, or by the hydrogenation of $CF_3CF=CFH$ as disclosed in U.S. Pat. No. 5,396,000, incorporated herein by reference.

The catalytic dehydrofluorination of HFC-245eb to produce both HFC-1234ze and HFC-1234yf is ordinarily carried out in the vapor phase using a dehydrofluorination catalyst. Vapor phase dehydrofluorination catalysts are well known in the art. These catalysts include, but are not limited to, alumina, aluminum fluoride, fluorided alumina, metal compounds on aluminum fluoride, metal compounds on fluorided alumina; oxides, fluorides, and oxyfluorides of magnesium, zinc and mixtures of magnesium and zinc and/or aluminum; lanthanum oxide and fluorided lanthanum oxide; chromium oxides, fluorided chromium oxides, and cubic chromium trifluoride; carbon, acid-washed carbon, activated carbon, three dimensional matrix carbonaceous materials; and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof.

In one embodiment of this invention, the catalytic vapor phase dehydrofluorination of HFC-245eb is carried out using fluorided alumina, aluminum fluoride or mixtures thereof as catalysts in a manner analogous to the dehydrofluorination of $CF_3CHFCHF_2$ to $CF_3CF=CHF$ as disclosed in U.S. Pat. No. 5,396,000, incorporated herein by reference. Fluorided alumina and aluminum fluoride can be prepared as described in U.S. Pat. No. 4,902,838, incorporated herein by reference or by treatment of alumina with a vaporizable fluorine containing compound such as $CF_2Cl_2$ as shown in the Examples below or treatment with compounds such as $CF_2HCl$ and $CHF_3$.

In other embodiments of this invention, the dehydrofluorination of HFC-245eb is carried out using carbon, activated carbon, or three dimensional matrix carbonaceous materials as catalysts in a manner analogous to the processes disclosed in U.S. Pat. No. 6,369,284, incorporated herein by reference; or using metals such as sodium, potassium, rubidium, cesium, yttrium, lanthanum, cerium, praseodymium, neodymium, samarium, chromium, iron, cobalt, rhodium, nickel, copper, zinc, and mixtures thereof, supported on carbon as catalysts in a manner analogous to the processes disclosed in U.S. Pat. No. 5,268,122, incorporated herein by reference. Carbon from any of the following sources are useful for the process of this invention; wood, peat, coal, coconut shells, bones, lignite, petroleum-based residues and sugar. Commercially available carbons which may be used in this invention include those sold under the following trademarks: Barneby & Sutcliffe™, Darco™, Nucharm™, Columbia JXN™, Columbia LCK™, Calgon PCB™, Calgon BPL™, Westvaco™, Norit™, and Barnaby Cheny NB™.

Carbon includes acid-washed carbon (e.g., carbon that has been treated with hydrochloric acid or hydrochloric acid followed by hydrofluoric acid). Acid treatment is typically sufficient to provide carbon that contains less than 1000 ppm of ash. Suitable acid treatment of carbon is described in U.S. Pat. No. 5,136,113, incorporated herein by reference. The carbon of this invention also includes three dimensional matrix porous carbonaceous materials. Examples are those described in U.S. Pat. No. 4,978,649, incorporated herein by reference. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

In a further embodiment of this invention, the catalytic dehydrofluorination of HFC-245eb is carried out using chromium oxides, fluorided chromium oxides, and cubic chromium trifluoride as catalysts. Cubic chromium trifluoride may be prepared from $CrF_3 \cdot XH_2O$, where X is 3 to 9, preferably 4, by heating in air or an inert atmosphere (e.g., nitrogen or argon) at a temperature of about 350° C. to about 400° C. for 3 to 12 hours, preferably 3 to 6 hours.

The physical shape of the catalyst is not critical and may, for example, include pellets, powders or granules. Additionally, for catalysts supported on carbon, the carbon may be in the form of powder, granules, or pellets, or the like. Although not essential, catalysts may be treated with HF before use. It is thought that this converts some of the surface oxides to oxyfluorides. This pretreatment can be accomplished by placing the catalyst in a suitable container (which can be the reactor to be used to perform the reaction of the instant invention) and thereafter, passing HF over the dried catalyst so as to partially saturate the catalyst with HF. This is conveniently carried out by passing HF over the catalyst for a period of time (e.g., about 15 to 300 minutes) at a temperature of, for example, about 200° C. to about 450° C.

The catalytic dehydrofluorination may be suitably conducted at a temperature in the range of from about 200° C. to about 500° C., and is preferably conducted at a temperature in the range of from about 300° C. to about 450° C. The contact time is typically from about 1 to about 450 seconds, preferably from about 10 to about 120 seconds.

The reaction pressure can be subatmospheric, atmospheric or superatmostpheric. Generally, near atmospheric pressures are preferred. However, the dehydrofluorination can be beneficially run under reduced pressure (i.e., pressures less than one atmosphere).

The catalytic dehydrofluorination can optionally be carried out in the presence of an inert gas such as nitrogen, helium, or argon. The addition of an inert gas can be used to increase the extent of dehydrofluorination. Of note are processes where the mole ratio of inert gas to hydrofluorocarbon undergoing dehydrofluorination is from about 5:1 to about 0.5:1. Nitrogen is the preferred inert gas.

Reaction products HFC-1234yf and HFC-1234ze and any unconverted HFC-245eb are recovered from the effluent leaving the reactor. The unconverted HFC-245eb can be recycled back to the reactor to produce additional HFC-1234yf and HFC-1234ze. In one embodiment of this invention, the unconverted HFC-245eb is recycled back to the reactor as it's azeotrope with HF. U.S. Publication No. 2009/0264690 A1, disclosing an azeotrope of HF/HFC-245eb, is incorporated herein in its entirety. U.S. Publication No. 2007/0100173 discloses an azeotrope of the E-isomer of HFC-1234ze and HF and a method to separate the HFC-1234ze from the azeotrope, and U.S. Publication No. 2007/0100175 discloses an azeotrope of HFC-1234yf and HF and a method to separate the HFC-1234yf from the azeotrope. HFC-1234ze may be recovered as a HF/HFC-1234ze azeotrope. Similarly, HFC-1234yf may be recovered as a HF/HFC-1234yf azeotrope. Pure HFC-1234ze and pure HFC-1234yf can be further recovered from their HF azeotropes by using methods similar to those described in U.S. Publication No. 2007/0100173 and U.S. Publication No. 2007/0100175, both of which are incorporated herein by reference.

The present invention also provides azeotrope or near azeotrope compositions comprising an effective amount of hydrogen fluoride combined with the Z-isomer of HFC-1234ze.

In connection with developing processes for the separation of the individual compounds produced from the dehydrofluorination reaction of HFC-245eb, it is noted that the Z-isomer of HFC-1234ze (as well as the E-isomer of HFC-1234ze, unconverted HFC-245eb and HFC-1234yf) each can be present as their respective azeotrope or near azeotrope with HF. The HF come from the dehydrofluorination reaction of HFC-245eb.

By effective amount is meant an amount, which, when combined with Z-HFC-1234ze, results in the formation of azeotrope or near azeotrope mixture. As recognized in the art, an azeotrope or a near azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

For the purpose of this discussion, near azeotrope composition (also commonly referred to as an "azeotrope-like composition") means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-near azeotrope compositions in which during boiling or evaporation, the liquid composition changes to a substantial degree.

Additionally, near azeotrope compositions exhibit dew point pressure and bubble point pressure with virtually no pressure differential. That is to say that the difference in the dew point pressure and bubble point pressure at a given temperature will be a small value. In this invention, compositions with a difference in dew point pressure and bubble point pressure of less than or equal to 3 percent (based upon the bubble point pressure) is considered to be a near azeotrope.

Accordingly, the essential features of an azeotrope or a near azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope or near azeotrope liquid composition is subjected to boiling at different pressures. Thus, an azeotrope or a near azeotrope composition may be defined in terms of the unique relationship that exists among the components or in terms of the compositional ranges of the components or in terms of exact weight percentages of each component of the composition characterized by a fixed boiling point at a specified pressure.

It is also recognized in the art that various azeotrope compositions (including their boiling points at particular pressures) may be calculated (see, e.g., W. Schotte Ind. Eng. Chem. Process Des. Dev. (1980) 19, 432-439). Experimental identification of azeotrope compositions involving the same components may be used to confirm the accuracy of such calculations and/or to modify the calculations at the same or other temperatures and pressures.

In accordance with this invention, compositions are provided which comprise the Z-isomer of HFC-1234ze and HF, wherein the HF is present in an effective amount to form an azeotropic combination with the Z-HFC-1234ze. According to calculations, these compositions comprise from about 77.0 mole percent to about 48.5 mole percent HF and from about 23.0 mole percent to about 51.5 mole percent Z-HFC-1234ze (which form azeotropes boiling at a temperature of from between about −20° C. and about 160° C. and at a pressure of from between about 4.75 psi (32.7 kPa) and about 997 psi (6874 kPa)).

Additionally, near azeotrope compositions containing HF and Z-HFC-1234ze may also be formed. Such near azeotrope compositions exist around azeotrope compositions. For example, with respect to the azeotropic composition calculated to comprise 77.0 mole percent HF and 23.0 mole percent Z-HFC-1234ze at −20° C. and 4.75 psi (32.7 kPa), other compositions comprising from about 80.2 mole percent to about 70.2 mole percent HF and from about 19.8 mole percent to about 29.8 mole percent Z-HFC-1234ze are considered to be near azeotrope compositions at same temperature and pressure. Similarly, with respect to the azeotropic composition calculated to comprise 61.3 mole percent HF and 38.7 mole percent Z-HFC-1234ze at 60° C. and 93.2 psi (643 kPa), other compositions comprising from about 67.8 mole percent to about 53.6 mole percent HF and from about 32.2 mole percent to about 46.4 mole percent Z-HFC-1234ze are considered to be near azeotrope compositions at the same temperature and pressure. Also similarly, with respect to the azeotropic composition calculated to comprise 49.9 mole percent HF and 50.1 mole percent Z-HFC-1234ze at 150° C. and 782 psi (5392 kPa), other compositions comprising from about 60.2 mole percent to about 35.4 mole percent HF and from about 39.8 mole percent to about 64.6 mole percent Z-HFC-1234ze are considered to be near azeotrope compositions at the same temperature and pressure.

Compositions may be formed that consist essentially of azeotrope combinations of hydrogen fluoride with Z-HFC-1234ze. These include compositions calculated to consist essentially of from about 77.0 mole percent to about 48.5 mole percent HF and from about 23.0 mole percent to about 51.5 mole percent Z-HFC-1234ze (which forms an azeotrope boiling at a temperature from between about −20° C. and about 160° C. and at a pressure from between about 4.75 psi (32.7 kPa) and about 997 psi (6874 kPa)).

It has been calculated that azeotropes of Z-HFC-1234ze and HF are formed at a variety of temperatures and pressures. For example, azeotrope compositions consisting essentially of Z-HFC-1234ze and HF may be formed between 32.7 kPa (at a temperature of −20° C.) and 6874 kPa (at a temperature of 160° C.), said compositions ranging from about 77.0 mole percent HF (and 23.0 mole percent Z-HFC-1234ze) to about 48.5 mole percent HF (and 51.5 mole percent Z-HFC-1234ze). An azeotrope of HF and Z-HFC-1234ze at 60.0° C. and 93.2 psi (643 kPa) has been calculated to consist essentially of about 61.3 mole percent HF and about 38.7 mole percent Z-HFC-1234ze. An azeotrope of HF and Z-HFC-1234ze at 150.0° C. and 782 psi (5392 kPa) has been calculated to consist essentially of about 49.9 mole percent HF and about 50.1 mole percent Z-HFC-1234ze.

The calculations for the azeotrope and near azeotrope compositions above are based on an 18° C. boiling point (at atmospheric pressure) data for Z-HFC-1234ze. Latest publications however show that the boiling point of Z-HFC-1234ze is at about 9° C. at atmospheric pressure. Based upon this updated Z-HFC-1234ze boiling point data of 9° C., new calculations show that Z-HFC-1234ze and HF form azeotropic compositions which comprise from about 68.1 mole percent to about 41.6 mole percent HF and from about 31.9 mole percent to about 58.4 mole percent Z-HFC-1234ze (which form azeotropes boiling at a temperature of from between about −20° C. and about 160° C. and at a pressure of from between about 5.92 psi (40.8 kPa) and about 929 psi (6404 kPa)).

Additionally, according to new calculations, near azeotrope compositions containing HF and Z-HFC-1234ze may also be formed. Such near azeotrope compositions exist around azeotrope compositions. For example, with respect to the azeotropic composition calculated to comprise about 68.1 mole percent HF and about 31.9 mole percent Z-HFC-1234ze at −20° C. and 5.92 psi (40.8 kPa), other compositions comprising from about 72.4 mole percent to about 50.4 mole percent HF and from about 27.6 mole percent to about 49.6 mole percent Z-HFC-1234ze are considered to be near azeotrope compositions at the same temperature and pressure. Similarly, with respect to the azeotropic composition calculated to comprise about 53.0 mole percent HF and about 47.0 mole percent Z-HFC-1234ze at 60° C. and 108.9 psi (751 kPa), other compositions comprising from about 59.6 mole percent to about 44.8 mole percent HF and from about 40.4 mole percent to about 55.2 mole percent Z-HFC-1234ze are considered to be near azeotrope compositions at the same temperature and pressure. Also similarly, with respect to the azeotropic composition calculated to comprise about 46.4 mole percent HF and about 53.6 mole percent Z-HFC-1234ze at 150° C. and 756 psi (5211 kPa), other compositions comprising from about 56.6 mole percent to about 33.4 mole percent HF and from about 43.4 mole percent to about 66.6 mole percent Z-HFC-1234ze are considered to be near azeotrope compositions at the same temperature and pressure.

According to new calculations, compositions may be formed that consist essentially of azeotrope combinations of hydrogen fluoride with Z-HFC-1234ze. These include compositions calculated to consist essentially of from about 68.1 mole percent to about 41.6 mole percent HF and from about 31.9 mole percent to about 58.4 mole percent Z-HFC-1234ze (which form azeotropes boiling at a temperature of from between about −20° C. and about 160° C. and at a pressure of from between about 5.92 psi (40.8 kPa) and about 929 psi (6404 kPa)).

New calculations also show that azeotropes of Z-HFC-1234ze and HF are formed at a variety of temperatures and pressures. For example, azeotrope compositions consisting essentially of Z-HFC-1234ze and HF may be formed between 40.8 kPa (at a temperature of −20° C.) and 6404 kPa (at a temperature of 160° C.), said compositions ranging from about 68.1 mole percent HF (and about 31.9 mole percent Z-HFC-1234ze) to about 41.6 mole percent HF (and about 58.4 mole percent Z-HFC-1234ze). An azeotrope of HF and Z-HFC-1234ze at 60.0° C. and 108.9 psi (751 kPa) has been calculated to consist essentially of about 53.0 mole percent HF and about 47.0 mole percent Z-HFC-1234ze. An azeotrope of HF and Z-HFC-1234ze at 150.0° C. and 756 psi (5211 kPa) has been calculated to consist essentially of about 46.4 mole percent HF and about 53.6 mole percent Z-HFC-1234ze.

The reactor, distillation columns, and their associated feed lines, effluent lines, and associated units used in applying the processes of this invention should be constructed of materials resistant to hydrogen fluoride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The following specific embodiments are to be construed as merely illustrative, and do not constrain the remainder of the disclosure in any way whatsoever.

EXAMPLES

Preparation of Fluorided Alumina Catalyst

A Hastelloy tube (1" OD×0.854 ID×10"L) was filled with 25 cc (16.68 g) gamma-alumina ground to 12-20 mesh. The packed portion of the reactor was heated by a 5.0"×1" ceramic band heater clamped to the outside of the reactor. A thermocouple, positioned between the reactor wall and the heater, measured the reactor temperature. The catalyst was dried by heating at 200° C. overnight under a nitrogen flow of 50 sccm ($8.33 \times 10^{-7}$ m$^3$/s). The nitrogen flow was then reduced to 5 sccm ($8.33 \times 10^{-8}$ m$^3$/s) and a flow of 20 sccm ($3.33 \times 10^{-7}$ m3/s) CFC-12 started and maintained for 60 minutes. The temperature was raised to 325° C. and held at this temperature for a further 60 minutes. The CFC-12 flow stopped and the reactor temperature raised to 400° C. under a flow of 50 sccm ($8.33 \times 10^{-7}$ m$^3$/s) of nitrogen and held at this temperature for an additional 60 minutes. The reactor was then brought to the desired operating temperature.

General Procedure for Product Analysis

The following general procedure is illustrative of the method used for analyzing the products of fluorination reactions. Part of the total reactor effluent was sampled on-line for organic product analysis using a gas chromatograph equipped a mass selective detector (GC/MS). The gas chromatography utilized a 20 ft. (6.1 m) long×⅛ in. (0.32 cm) diameter tube containing Krytox® perfluorinated polyether on an inert carbon support. The helium flow was 30 mL/min ($5.0 \times 10^{-7}$ m$^3$/sec). Gas chromatographic conditions were 60° C. for an initial hold period of three minutes followed by temperature programming to 200° C. at a rate of 6° C./minute.

LEGEND

1234yf is $CF_3CF = CH_2$
1234ze is E and Z—$CF_3CH = CHF$
245eb is $CF_3CHFCH_2F$ Example 1

Dehydrofluorination of HFC 245eb to HFC-1234ze and HFC-1234yf

To the reactor containing the fluorided alumina catalyst prepared as above was fed a vapor of HFC-245eb and nitrogen at various reactor temperatures. The nitrogen to HFC-245eb ratio was 0.67:1 and the contact time was 36 seconds for the first four analyses. For the fifth analysis, the nitrogen to HFC-245eb ratio was 1:1 and the contact time was 90 seconds. The product leaving the reactor was analyzed by GC/MS and the results in mole % are summarized in Table 1.

TABLE 1

| Reactor T ° C. | 1234yf | E-1234ze | Z-1234ze | 245eb |
|---|---|---|---|---|
| 200 | ND | ND | ND | 99.9 |
| 300 | 14.3 | 3.6 | 0.8 | 81.2 |
| 350 | 28.2 | 9.5 | 2.3 | 60.0 |
| 400 | 45.4 | 18.9 | 4.4 | 31.3 |
| 400 | 52.0 | 22.0 | 5.4 | 20.4 |

ND = Not detected

What is claimed is:
1. An azeotropic composition comprising:
   (a) Z—$CF_3CH = CHF$ and
   (b) HF; wherein the HF is present in an effective amount to form an azeotropic combination with the Z—$CF_3CH = CHF$.
2. An azeotropic composition consisting essentially of:
   (a) Z—$CF_3CH = CHF$ and
   (b) HF; wherein the HF is present in an effective amount to form an azeotropic combination with the Z—$CF_3CH = CHF$.
3. A near azeotrope composition comprising:
   (a) Z—$CF_3CH = CHF$ and
   (b) HF; wherein the HF is present in an effective amount to form a near azeotrope combination with the Z—$CF_3CH = CHF$.

* * * * *